(12) United States Patent
King

(10) Patent No.: US 8,993,759 B2
(45) Date of Patent: Mar. 31, 2015

(54) TRANSAMINATION OF NITROGEN-CONTAINING COMPOUNDS TO MAKE CYCLIC AND CYCLIC/ACYCLIC POLYAMINE MIXTURES

(75) Inventor: Stephen W. King, League City, TX (US)

(73) Assignee: DOW Global Technologies LLC, Midland, MI (US)

( * ) Notice: Subject to any disclaimer, the term of this patent is extended or adjusted under 35 U.S.C. 154(b) by 0 days.

(21) Appl. No.: 13/884,430

(22) PCT Filed: Oct. 20, 2011

(86) PCT No.: PCT/US2011/057045
§ 371 (c)(1),
(2), (4) Date: May 9, 2013

(87) PCT Pub. No.: WO2012/064483
PCT Pub. Date: May 18, 2012

(65) Prior Publication Data
US 2013/0231476 A1 Sep. 5, 2013

Related U.S. Application Data

(60) Provisional application No. 61/412,026, filed on Nov. 10, 2010.

(51) Int. Cl.
| | | |
|---|---|---|
| *C07D 241/04* | (2006.01) | |
| *C07D 243/08* | (2006.01) | |
| *C07D 295/023* | (2006.01) | |
| *C07D 295/13* | (2006.01) | |
| *C07C 209/02* | (2006.01) | |
| *C07C 209/48* | (2006.01) | |
| *C07C 209/60* | (2006.01) | |

(52) U.S. Cl.
CPC .......... *C07D 295/023* (2013.01); *C07D 243/08* (2013.01); *C07D 295/13* (2013.01)
USPC ........... 544/358; 544/402; 540/575; 564/470; 564/512

(58) Field of Classification Search
CPC .................................................. C07D 295/023
See application file for complete search history.

(56) References Cited

U.S. PATENT DOCUMENTS

| | | | | |
|---|---|---|---|---|
| 2,267,686 A | * | 12/1941 | Kyrides | 544/358 |
| 2,454,404 A | * | 11/1948 | Pfann et al. | 544/358 |
| 2,809,195 A | * | 10/1957 | Miller | 544/358 |
| 2,901,482 A | * | 8/1959 | Mackenzie et al. | 544/358 |
| 3,120,524 A | * | 2/1964 | Godfrey | 544/404 |
| 3,285,920 A | * | 11/1966 | Muhlbauer et al. | 544/352 |
| 4,552,961 A | | 11/1985 | Herdle | |
| 4,568,746 A | | 2/1986 | Cowherd, III | |
| 4,584,405 A | | 4/1986 | Vanderpool | |
| 4,602,091 A | | 7/1986 | Brennan | |
| 4,806,517 A | | 2/1989 | Vaderpool et al. | |
| 4,906,782 A | | 3/1990 | Hara et al. | |
| 4,922,024 A | | 5/1990 | Bowman et al. | |
| 4,927,931 A | | 5/1990 | Molzahn et al. | |
| 4,983,735 A | | 1/1991 | Hartwell et al. | |
| 5,030,740 A | | 7/1991 | Bowman et al. | |
| 5,073,635 A | | 12/1991 | Bowman et al. | |
| 5,222,599 A | | 6/1993 | Boyce | |
| 5,248,827 A | | 9/1993 | Hara et al. | |
| 5,256,786 A | | 10/1993 | Bowman et al. | |
| 5,455,352 A | | 10/1995 | Huellmann et al. | |
| 6,362,332 B1 | * | 3/2002 | Merger et al. | 540/538 |
| 6,362,333 B1 | * | 3/2002 | Merger et al. | 540/539 |
| 6,465,601 B1 | | 10/2002 | Wiesendanger et al. | |
| 6,534,441 B1 | | 3/2003 | Bartley et al. | |
| 7,053,247 B2 | | 5/2006 | Lif et al. | |
| 2005/0095189 A1 | | 5/2005 | Brey et al. | |
| 2010/0087681 A1 | | 4/2010 | Petraitis et al. | |
| 2010/0087682 A1 | | 4/2010 | King et al. | |
| 2010/0087683 A1 | | 4/2010 | Cook et al. | |
| 2010/0087684 A1 | | 4/2010 | Do et al. | |
| 2010/0094007 A1 | | 4/2010 | King et al. | |
| 2010/0094008 A1 | | 4/2010 | King et al. | |
| 2010/0137642 A1 | | 6/2010 | King et al. | |
| 2013/0225864 A1 | | 8/2013 | King | |

FOREIGN PATENT DOCUMENTS

| | | |
|---|---|---|
| GB | 1 508 460 | 4/1978 |
| GB | 1551127 | 8/1979 |
| JP | 2006-306790 | 11/2006 |
| RU | 2186761 | 8/2002 |
| RU | 2226188 | 3/2004 |
| WO | WO 03/010125 | 2/2003 |
| WO | WO 2012/064484 | 5/2012 |

OTHER PUBLICATIONS

Reichle, "Reactions of Aliphatic a-w-Diamines in H+-Pentasils," Journal of Catalysis 11, pp. 556-568, 1993.
Wang et al., "Intermolecular condensation of ethylenediamine to 1,4-diazabiyclo(2,2,2)octane over H-ZSM-5 catalysts: Effects of Si/Al ratio and crystal size," Applied Catalysis A: General, vol. 379, Nos. 1-2, pp. 45-53, 2010.
Martin W.B. et al., "Preparation of piperazine," Journal of the American Chemical Society, pp. 1817-1818, XP-002666009, 1948, vol. 70.
Anderson et al., "Catalytic Synthesis of Aziridine From 1,2-Diaminoethane," Chemistry of Heterocyclic Compounds, vol. 29, No. 10. pp. 1134-1141, XP-002666010, 1993.
Ishiguro et al, "Synthesis of Piperazines. XII Synthesis of Homopiperazine," vol. 79, No. 2, pp. 153-156, XP-002666011, 1959.
Zheng Jing-zhi, "N-Benzylation of phthalimide under the catalytic action of A1__2O__3 supported KF reagent" (Department of Chemical Engineering and Pharmacy, Wuhan Institute of Chemical Technology, Wuhan 430073), Huaxue Shiji , 2003, 25(5), 311-312.
Wang et al., "A Continuous Process for the Synthesis of Homopiperazine Catalyzed by Cu-Based Catalysts" React. Kinet. Catal. Lett., vol. 89, No. 2, pp. 201-208, 2006.

* cited by examiner

*Primary Examiner* — Brian J Davis
(74) *Attorney, Agent, or Firm* — Kagen Binder, PLLC

(57) ABSTRACT

A transamination process is described to prepare polyamine product mixtures from reactants comprising mixed nitrogen-containing compounds with binary carbon spacing between nitrogen-containing groups (a binary component). A second nitrogen-containing component with a second carbon atom spacing between nitrogen-containing groups may also be employed. The molar ratio between the binary and second components can be adjusted to customize the product composition for desired end uses.

13 Claims, No Drawings

TRANSAMINATION OF NITROGEN-CONTAINING COMPOUNDS TO MAKE CYCLIC AND CYCLIC/ACYCLIC POLYAMINE MIXTURES

FIELD OF THE INVENTION

This application claims the benefit from International No. PCT/US20111057045, which was granted an International Filing date of Oct. 20, 2011, which in turn claims the benefit of U.S. Provisional Patent Application Ser. No. 61/412,026, filed Nov. 10, 2010, entitled TRANSAMINATION OF NITROGEN-CONTAINING COMPOUNDS TO MAKE CYCLIC AND CYCLIC/ACYCLIC POLYAMINE MIXTURES, which applications are incorporated herein by reference in their entireties.

The present invention relates to processes that use transamination to prepare amine product mixtures from reactants comprising nitrogen-containing compounds with a binary component having a binary carbon atom spacing between non-tertiary amine groups and, optionally, a second component having a carbon atom spacing between nitrogen-containing groups. The molar ratio between the binary component and the optional second component can be adjusted to customize the product composition for desired end uses.

BACKGROUND OF THE INVENTION

Transamination is a transfer of an amino group from one chemical compound to another, or the transposition of an amino group within a chemical compound. Transamination can be used to prepare amine compounds and mixtures of amine compounds from lower molecular weight nitrogen-containing compounds such as amines or nitriles. Transamination can provide acyclic and/or cyclic amine products. GB Patent No. 1508460 describes the transamination of ethylenediamine (EDA). U.S. Pat. Nos. 4,568,746 and 7,053,247 also describe the transamination of EDA. GB Patent No. 1551127 describes the transamination of 1,3-diaminopropane (1,3-DAP). JP 2006/306790 reacts 1,3-DAP with ethylene glycol in the presence of a dehydration catalyst such as activated alumina at 300C to obtain homopiperazine (hPIP) at 24% yield. The technical literature describes making hPIP from a mixture of EDA and 1,3-dibromopropane. See Huaxue Shiji, 2006, 28(5), 311-312. U.S. Pat. Nos. 6,465,601 describes the preparation of mixed amines by the transamination of a substituted phenolic compound (Mannich base) with another amine. The mixed amines are useful as accelerators for curable epoxy and polyurethane systems.

Although transamination has proved itself as a viable way to manufacture amines on the industrial scale, several challenges remain. First, the ability to customize product mixtures for desired end uses can be limited. Additionally, some processes produce mixtures whose cyclic content or acyclic content cannot be controlled easily to provide a product mix that can improve the end-use performance for a given application. Still, other processes must decompose higher members of the series by recycle to the dimers and trimers. Cyclic species are desired for many applications. For example, hPIP content is useful in epoxy curing applications as well as in lube oil and fuel compositions. Yet, other processes produce hPIP at low yields or produce byproduct salts that must be disposed of. It would be desirable to have a process that could vary the cyclic/acyclic mixture of amines that could be customized for a given end-use application from readily available starting materials.

SUMMARY OF THE INVENTION

The present invention provides improved strategies for using transamination techniques to prepare cyclic and cyclic/acyclic polyamine product mixtures. The present invention is based in part upon using a reaction composition that employs one or more mixed nitrogen-containing reactants. The mixed nitrogen-containing reactants comprise one or more nitrogen-containing compounds that have at least two non-tertiary amine groups separated from one another by binary carbon atom spacing (C2 spacing) and, optionally, at least two nitrogen-containing groups separated from one another by a second carbon atom spacing. The carbon atom spacing may be provided either in a single compound or in separate compounds. Additionally, the second carbon atom spacing may have a binary or other carbon atom spacing (e.g., a unitary (C1) or greater spacing).

As used herein, the term "carbon atom spacing" refers to the number of carbon atoms between nitrogen-containing groups of the nitrogen-containing compounds. For example, when the nitrogen-containing groups are amine groups, the term binary spacing refers to amine groups separated by a backbone spacing of two carbon atoms, and the term ternary spacing refers to amine groups separated by a backbone spacing of three carbon atoms.

As used herein, the term polyamine refers to a compound that includes at least two amine groups. With respect to a nitrogen-containing reactant that comprises a polyamine, at least two amine groups of the reactant are non-tertiary. Thus, at least two amine groups of a polyamine reactant can be primary, secondary, or a combination thereof. As long as a polyamine reactant includes at least two non-tertiary amine groups, the reactant optionally may also include tertiary amine group(s) as well.

As used herein, the term cyclic refers to a polyamine product mixture that comprises at least about 1% by weight of cyclic product, preferably at least about 5% by weight, more preferably at least about 10% by weight.

The polyamine products made using methods of the present invention may include two, or more primary, secondary, and/or tertiary amine groups, or combinations thereof. Preferred polyamine reactants are primary diamines.

The nature of the polyamine product composition made using the methods of the present invention can be easily customized for desired end uses simply by adjusting the molar ratio between the nitrogen-containing components of the reaction composition. In some cases, the molar ratio can be selected to favor product mixtures that include relatively greater amounts of cyclic materials. When using certain reactants, this strategy can be used to create product mixtures with significant quantities of hPIP and compounds having hPIP moieties. In other instances, the molar ratio can be selected to favor product mixtures that include relatively greater amounts of acyclic materials. The practice of the invention can be used to prepare compositions containing novel polyamine congener products, such as congeners of triamines, tetramines, or other polyamines. As used herein, congeners of polyamine products are variants, or different configurations of the polyamine product(s), that contain the same number of N atoms.

The methodology of the invention provides the production of mixed polyamines useful for a variety of end-use applications and offers much better control over the resultant product composition as compared to using only one reactant alone.

In one aspect, the present invention relates to a method of making a cyclic polyamine-containing polyamine mixture comprising the steps of:

(a) providing a reaction composition comprising one or more nitrogen-containing compounds having a binary component that has at least two non-tertiary amine groups separated from one another by a binary carbon atom spacing (C2 spacing), and, optionally, a second component that has at least two nitrogen-containing groups separated from one another by a second carbon atom spacing; and (b) subjecting the reaction composition to a transamination reaction in the presence of a hydrogenation/dehydrogenation catalyst to obtain the cyclic polyamine-containing mixture.

In another aspect, the present invention relates to a method of making a cyclic polyamine-containing product mixture comprising the steps of (a) providing information indicative of a transamination product mixture composition as a function of a molar ratio of a reaction composition having a binary component that has at least two non-tertiary amine groups separated from one another by a binary carbon atom spacing (C2 spacing), and a second component that has at least two nitrogen containing groups separated from one another by a second carbon atom spacing; and (b) using the information to provide the reaction mixture; and (c) subjecting the reaction mixture to a transamination reaction in the presence of a hydrogenation/dehydrogenation catalyst.

In another aspect, the present invention relates to a method of making homopiperazine and/or homopiperazine moieties comprising the steps of:

(a) providing a reaction composition comprising (i) $H_2NCH_2CH_2NHCH_2CH_2CH_2NH_2$, or $H_2NCH_2CH(CH_3)NHCH_2CH_2CH_2NH_2$, or a mixture thereof, or (ii) a mixture of 1,3-diaminopropane and ethylenediamine; or (iii) a mixture of 1,3-diaminopropane and 1,2-propanediamine and (b) (b) subjecting the reaction composition to a transamination reaction in the presence of a hydrogenation/dehydrogenation catalyst to obtain a product mixture comprising homopiperazine and/or homopiperazine moieties.

In another aspect, the present invention relates to a method of making a cyclic polyamine-containing product mixture wherein the reaction composition comprises at least a first nitrogen-containing compound comprising a binary component that has at least two non-tertiary amine groups separated from one another by a binary carbon atom spacing (C2 spacing) and, a second nitrogen-containing compound comprising a second component that has (i) at least two non-tertiary amine groups separated from one another by a ternary carbon atom spacing (C3 spacing), (ii) at least two nitrile functionalities separated by a unitary carbon atom spacing (C1 spacing), (iii) at least one nitrile functionality and one non-tertiary amine functionality separated from one another by a binary carbon atom spacing (C2 spacing), or (iv) a combination thereof.

In another aspect, the present invention relates to a method of making a polyamine-containing product mixture comprising polyamine congeners of triamines, such as diethylenetriamine (DETA), and tetramines, such as triethylenetetramine (TETA).

In another aspect, the present invention relates to a method of making a cyclic polyamine-containing mixture wherein the molar ratio of the binary component to the non-binary component is in the range from about 10:1 to about 0.1:10, optionally about 0.9:1 to about 2:1; optionally about 1:1.

In another aspect, the present invention relates to a method of making a predominantly acyclic polyamine-containing mixture wherein the molar ratio of the binary component to the second component is in less than about 1:1, optionally less than about 1:2, optionally less than about 1:3, optionally less than about 1:4.

In another aspect, the present invention relates to a mixture of polyamines obtained by the method of the invention.

DETAILED DESCRIPTION OF PRESENTLY PREFERRED EMBODIMENTS

Reference will now be made in detail to representative embodiments of the invention. While the invention will be described in conjunction with the enumerated embodiments, it will be understood that they are not intended to limit the invention to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods and materials described.

All publications and patents mentioned herein are incorporated herein by reference in their respective entireties for the purpose of describing and disclosing, for example, the constructs and methodologies that are described in the publications which might be used in connection with the presently described invention.

Unless defined otherwise herein, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

In an aspect of the invention, the nitrogen-containing reactant having the binary component is a polyamine that may be represented by the formula

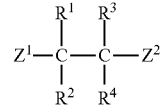

FORMULA I wherein $Z^1$ and $Z^2$ are independently primary or secondary amines; and $R^1$, $R^2$, $R^3$, and $R^4$ are, independently H or substituted and unsubstituted hydrocarbyl.

Hydrocarbyl groups that may be used in the present invention include linear, branched, or cyclic hydrocarbyl such as alkyl, aryl, aralkyl, or the like; a monovalent moiety including one or more heteroatoms; polyether chains comprising one or more oxyalkylene repeating units such as —$R^5O$—, wherein. $R^5$ is often alkylene of 2 to 5 carbon atoms; other oligomeric or polymer chains of at least 2 repeating units; —$R^6NR^1R^2$— wherein $R^1$ and $R^2$ are as defined above, and $R^6$ is alkylene of at least 2, preferably 2 to 5 carbon atoms. Preferably, each of the $R^1$ through $R^4$ independently is H or straight, branched, or cyclic hydrocarbyl such as alkyl of 1 to 10 carbon atoms, preferably 1 to 3 carbon atoms. More preferably, each of $R^1$ through $R^4$ is H.

A preferred binary spacing group for use in FORMULA I has the formula

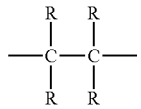

FORMULA II wherein each R is independently a monovalent moiety or co-member of a ring structure with one or more other R groups or N-substituents that is generally inert to reaction with amine groups under the transamination conditions to be used. Each R independently may be H, linear branched, cyclic, substituted, unsubstituted, aliphatic, aromatic, saturated, and/or unsaturated. In some embodiments, any R independently may be an oligomeric and/or polymeric chain grafted or otherwise linked to the atoms. Exemplary grafts may be, for instance, polyurethane, poly(meth)acrylic, polyester, polyolefin, polyether, fluorinated, combinations of these, and the like. In other exemplary embodiments, each R is independently H, a hydrocarbyl of 1 to 20 carbon atoms, a group containing a hetero atom, such as an ether moiety, or a primary or secondary amine moiety having the formula— $R^1R^2$ wherein $R^1$ and $R^2$ are as defined above, including one or more hetero atoms and from 1 to 50 carbon atoms; substituted or unsubstituted aryl, or the like. More preferably, each R is independently H, a hydrocarbyl of 1 to 4 carbon atoms, or an ether of 1 to 4 carbon atoms. Most preferably, each R is H or methyl or ethyl.

Examples of useful polyamines with binary (C2) spacing between first and second non-tertiary amine groups include ethylenediamine (EDA), propylenediamine (also referred to as 1,2-propanediamine or PDA), 1,2-cyclohexanediamine; 2-methyl-1,2-propanediamine; 2-ethyl, 1-2-butanediamine; 1,2-butanediamine; 1,2-octanediamine; combinations of these, and the like. EDA is most preferred. The C2 spacing groups may be portions of larger structures that may be acyclic, cyclic, branched, linear, substituted, unsubstituted, aliphatic, aromatic, saturated, and/or unsaturated. An example of a polyamine that has both binary and ternary spacing in the molecule is $H_2NCH_2CH_2NHCH_2CH_2CH_2NH_2$. Other such mixed binary and ternary polyamines are known and include $H_2NCH_2CH(CH_3)NHCH_2CH_2CH_2NH_2$, and $NH_2CH_2CH_2NHCH(CH_3)CH_2CH_2NH_2$.

In an aspect of the invention, a second nitrogen-containing component may be employed. The second nitrogen-containing component preferably has at least two functional groups that have (i) at least two non-tertiary amine groups separated from one another by a ternary carbon atom spacing (C3 spacing), (ii) at least two nitrile functionalities separated by one carbon atom (C1 spacing), (iii) at least one nitrile functionality and one non-tertiary amine functionality separated from one another by a binary carbon atom spacing (C2 spacing), or (iv) a combination thereof.

Examples of nitrogen-containing second components reactants include nitriles and polyamines. Preferred nitriles may be represented by FORMULA III.

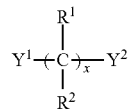

FORMULA III wherein $Y^1$ and $Y^2$ are each CN and x is an integer of from 1 to about 10, preferably from 1 to about 5; most preferably 1; or $Y^1$ is CN and $Y^2$ is independently a non-tertiary amine and x is an integer of from 2 to about 10, preferably from 2 to about 5; most preferably 2; and $R^1$ and $R^2$ are as defined above.

Preferred polyamine second reactants may be represented by FORMULA IV.

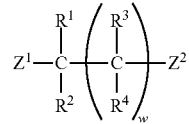

FORMULA IV wherein $Z^1$ and $Z^2$ are independently primary or secondary amines;

$R^1$, $R^2$, $R^3$ and $R^4$ are as defined above; and w is an integer of 2 or more, preferably from 2 to about 10, more preferably from about 2 to about 5.

The spacing groups utilized in the second nitrogen-containing component, may be portions of larger structures that may be branched, linear, substituted, unsubstituted, aliphatic, aromatic, saturated, and/or unsaturated. A preferred spacing group for a polyamine second component is a C3 moiety that has the formula

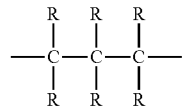

FORMULA V wherein each R is as defined above with respect to Formula II.

Examples of useful nitrile compounds useful as the second component include dinitriles, aminonitriles, and combinations thereof. Specific examples of useful nitriles include malononitrile, succinonitrile, glutaronitrile, adiponitrile, 2-aminoacetonitrile, 3-aminopropanenitrile, 4-aminobutanenitrile, 2-methylmalononitrile, and 2-methylsuccinonitrile.

Examples of polyamines useful as the second component include 1,3-diaminopropane (1,3-DAP), 1,3-pentanediamine; 1,3-butanediamine; 2,2-dimethyl-1,3-propanediamine; 2,2-diethyl-1,3-propanediamine; 1,3-diamino-2-phenylpropane; 2-(aminomethyl)-2-methyl-1,3-propanediamine; 1,4-diaminobutane; 1,5-diaminopentane; hexamethylenediamine; combinations of these, and the like. 1,3-DAP is most preferred. The spacing groups may be portions of larger structures that may be acyclic, cyclic, branched, linear, substituted, unsubstituted, aliphatic, aromatic, saturated, and/or unsaturated.

In preferred reaction mixture embodiments, the first component comprises a first polyamine that includes at least ethylenediamine (EDA) having a C2 spacing between amine groups, and a second polyamine that includes at least 1,3-DAP having a C3 spacing between amine groups.

Transamination of the reaction composition according to the practice of the invention results in a product mixture that includes many useful polyamine products. These include polyamine products that are primarily cyclic, although a mixture of cyclic and acyclic products may also be present. Polyamine products can be tri-, tetra, or higher amines, and generally include binary and/or ternary spacing between the amine groups.

In the modes of practice of the invention in which a mixture of EDA and 1,3-DAP are subjected to transamination, exemplary acyclic amine products include triamine congeners: diethylenetriamine (DETA), N-(2-aminoethyl)-1,3-propanediamine, and dipropylenetriamine, tetraamine congeners: triethylenetetramine (TETA), N,N'-bis(3-aminopropyl)ethylenediamine, 1-(2-aminoethyl)dipropylenetriamine, N1-[2-[(2-aminoethyl)amino]ethyl]-1,3-propanediamine, N,N'-bis(2-aminoethyl)-1,3-propanediamine, and tripropylenetetramine; and several pentamine congeners.

Examples of cyclic products include piperazine (PIP), homopiperazine (hPIP), N-2-aminoethylpiperazine (AEP), N-3-aminopropylpiperazine, N,N'-bis-(2-aminoethyl)-piperazine (DAEP), N,N'-bis-(3-aminopropyl)piperazine, N-2-aminoethyl-N'-3-aminopropylpiperazine, N-[2-(1-piperazinyl)ethyl]ethylenediamine (PEEDA), N-2-aminoethylhomopiperazine, N-3-aminopropylhomopiperazine, N-2-aminoethyl-N'-3-aminopropylhomopiperazine and the like.

Advantageously, transamination of mixtures of nitrogen-containing components such as nitriles and polyamines with binary and ternary spacing may be carried out to provide significant quantities of cyclic products in the product mixture. The cyclic products include significant amounts of cyclic amines having 6 and 7-membered rings with binary and/or ternary spacing between amine groups in the cyclic ring. For example, a mixture of EDA and 1,3-DAP may form significant quantities of piperazine and homopiperazine (hPIP).

The present invention can be practiced to provide amine mixtures with significant cyclic content. This is very advantageous as there are many uses where cyclic content in the product mix is strongly desired. Amine mixtures containing cyclic materials have shown benefits when used in epoxy curing agents and/or in oil and fuel additives. Other exemplary uses for product mixtures of the invention include other polymer curing, hydrocarbon purification, corrosion inhibitors, catalysts, surface activation, asphalt compositions, mineral processing aids, fabric softeners, textile additives, surfactants, catalysts, paper sizing compositions, etc.

The present invention may be carried out to favor the formation of cyclic products. For example, a polyamine having binary spacing (e.g., a C2 link in the case of a material such as EDA or PDA) can self-cyclize via transamination to form a cyclic diamine with a 6-membered ring. In the case of EDA, this cyclization via transamination yields piperazine.

It is true that a polyamine such as EDA can be self-cyclized to PIP when transaminated on its own, but no homopiperazine or other cyclic amine with a 7-membered ring is formed since only an amine with binary spacing is available as a reactant. Yet, when a polyamine such as EDA is subjected to transamination in the presence of a polyamine with ternary spacing such as 1,3-DAP, the polyamine with binary spacing can self-cyclize with itself to form a piperazine moiety, and additionally, the two kinds of polyamines can also react with each other to form substituted or unsubstituted cyclic amines having a 7-membered ring with N atoms at the 1 and 4 positions.

Thus, on one side of the ring, the nitrogen atoms are spaced by a C2 moiety. On the other side of the ring, the nitrogen atoms are spaced by a C3 moiety. Such substituted or unsubstituted cyclic amines shall be referred to as hPIP derivatives, wherein the C2 moiety, C3 moiety, or N atoms may be substituted or unsubstituted by groups such as R, $R^1$, and/or $R^2$ as defined above. An unsubstituted hPIP derivative includes only H as substituents of the C2 moiety, C3 moiety, and N atoms. The unsubstituted derivative is hPIP itself.

Theoretically, one or more polyamines with ternary spacing (e.g., a cyclization in which 1,3-DAP reacts with itself) could self or co-react, as the case may be, to form a cyclic polyamine with an 8-membered ring. However, 8-membered rings are thermodynamically disfavored compared to 6-and 7-membered rings. Accordingly, transamination of only amine(s) with ternary spacing would be expected to yield little if any amine product having an 8-membered ring. Rather, transamination of only amines(s) with ternary spacing primarily forms acyclic, high molecular weight amine products. See Applicant's co-pending application filed on Nov. 10, 2010, titled TRANSAMINATION OF N-CONTAINING COMPOUNDS TO HIGH MOLECULAR WEIGHT POLYALKYLENEAMINES, USSN 61/412,029, published as WO 2012/1064484, on May 18, 2012. However, a reaction mixture including a mixture of polyamines with binary and ternary spacing readily forms cyclic polyamines with 6 and 7-membered rings, but little if any formation of 8-membered rings occurs.

The molar ratio of first nitrogen-containing reactants subjected to transamination can vary over a wide range. However, the molar ratio of binary spaced and ternary spaced reactants is a significant factor impacting the composition of the product mixture that results upon transamination. For example, cyclic products can be formed when using a reactant mixture in which the molar ratio of the binary component such as one or more polyamines with binary spacing to the second component, such as one or more polyamines that preferably have ternary spacing is in the range of from about 0.1:1 to from about 10:1, preferably in the range of from about 0.5:1 to about 5:1. A mixture of 6 and 7-membered cyclic products are particularly favored when using reactant mixtures in which approximately equimolar amounts of polyamines with binary and ternary spacing are used. For example, the formation of cyclic products can be favored when the molar ratio of polyamine(s) with binary spacing to the polyamine(s) with ternary spacing is in the range from about 0.7:1 to about 3:1, preferably about 0.8:1 to about 2:1, more preferably about 0.9:1 to about 2:1, more preferably about 1:1.

On the other hand, if it is more desired to maximize the amount of acyclic amine products while minimizing cyclic content, a molar ratio of polyamine(s) with binary spacing to the polyamine(s) with ternary spacing should be less than 1:1 preferably less than about 1:2; more preferably less than about 1:3; and even more preferably less than about 1:4.

By changing the molar ratio within such ranges, product mixtures with customized compositions suiting a desired end use may be obtained. Thus, information can be obtained that is indicative of the product composition that results, desirably for a given set of transamination conditions, as a function of the binary to the secondary components over a suitable molar ratio range. Using this information, transamination can be practiced using a molar ratio effective to provide a desired product composition. Molar ratios can be selected that favor the formation of cyclic products. Alternatively, molar ratios can be selected to favor the formation of acyclic products, subject to the molar ratios described above. Adjustment of other reaction conditions can also be used to help customize the product mixture. Examples of other reaction conditions that can be used to customize product compositions include the nature of the catalyst, the concentration of catalyst on its carrier in the case of heterogeneous catalysts, the physical form of the catalyst, the pressure of the reaction, the concentration of $H_2$ during the reaction, conversion, temperature, recycle, combinations of these, and/or the like.

Useful carrier materials can be described in terms of their carrier portion size, more particularly, average carrier portion size. Average carrier portion size can be described as the average longest or length dimension of the carrier material. Average carrier portion size can be determined by taking multiple representative samples and physically measuring the carrier material sizes found in representative samples. Such samples may be taken by various characterization techniques, such as by scanning electron microscopy (SEM). In some aspects, the carrier portion can be provided in the form of an extrudate. Extrudates ranging in diameter of about 1/8" (3.175 mm) or less can be useful, for example in the range of about 1/32" (0.79375 mm) to about 1/8". Extrudates having a diameter of about 1/16" (1.5875 mm) are preferred.

The product mixture resulting from transamination can be used as is, packaged stored, or modified as desired depending upon the desired end use. In one mode of practice, the product mixture may include amine products with a range of volatilities. If a limited VOC specification is applicable, more volatile components can be removed before the remainder is used, stored, or otherwise handled. If a limited viscosity specification is applicable, more viscous components can be obtained by refining the more volatile (less viscous) components before the remainder is used, stored, or otherwise handled. Components that are removed, and even some by-products, have commercial value and may have many uses. These include being recycled as a feed for the transamination reaction, refined to recover some of the product(s) in more pure form, used as reactants in other reactions, used as is or with any desired modification as products such as epoxy curing agents, combinations of these, and the like. Different components of the product mixture may have different uses, and so the product mixture can be separated into these components based upon the desired end use.

Transamination of reaction compositions according to the invention may be carried out in a variety of ways. In accordance with a preferred mode of practice, the reactants are combined and caused to react in a suitable reactor volume in the presence of a suitable catalyst under temperature and pressure conditions effective to cause the transamination reaction.

The methods of the invention can be practiced in any suitable reactor. These include batch reactors, continuous fixed bed reactors, slurry bed reactors, fluidized bed reactors, catalytic distillation reactors, combinations of these, and the like.

A variety of catalysts can be used in the practice of the present invention for transamination. Catalysts can be acidic, alkaline, neutral, or a combination of different catalysts can be used. Representative classes include catalyst metals, alloys, intermetallic compositions, or metal salts (such as oxides, nitrides, phosphates, silicates, and the like), or mixtures of one or more transition metals, including the lanthanoid and/or actinoid series. A wide variety of catalysts applicable to amine chemistry are described in U.S. Pat. Nos. 6,534,441; 5,256,786; 5,073,635; 5,030,740; 4,927,931; 5,222,599; 4,906,782; 4,922,024; 4,806,517; 4,584,405; 4,552,961; 5,455,352; 5,248,827; 4,602,091. See also Russian patents 2226188 and 2186761. The catalyst(s) can be present as metals, alloys, mixtures, intermetallic compositions, as compounds such as oxides, hydroxides, salts, alkoxides, silicates, phosphates, as complexes, or the like, supported or unsupported.

In a preferred embodiment, the catalyst incorporates one or more hydrogenation and/or dehydrogenation catalysts. Hydrogenation generally refers to a chemical reaction involving the addition of hydrogen, and the process is often used to reduce or saturate organic materials. The reverse reaction in which hydrogen is removed from an organic molecule is referred to as dehydrogenation. The use of hydrogenation and/or dehydrogenation catalysts has been found to be useful for transamination and in the practice of the present invention.

A wide variety of hydrogenation/dehydrogenation catalysts are known. Platinum group metals, particularly platinum, palladium, rhodium, and ruthenium form highly active hydrogenation/dehydrogenation catalysts. These are known to operate at lower temperatures and lower pressures of $H_2$. Non-precious metal catalysts, especially those based on nickel (such as Raney nickel and Urushibara nickel) have also been developed as economical alternatives. Other hydrogenation/dehydrogenaton catalysts might incorporate iron, copper, chromium, molybdenum, cobalt, osmium, iridium, and/or the like.

In particularly preferred embodiments, the catalytically active material incorporates hydrogenation/dehydrogenation catalytic ingredients comprising nickel and rhenium. The weight ratio of nickel to rhenium may vary over a wide range. For instance, the weight ratio of nickel to rhenium may be in the range from about 1:1000 to 1000:1, preferably 1:100 to 100:1, more preferably 1:50 to 50:1. Even more desirably, the weight ratio of nickel to rhenium is within these ranges with the proviso that the weight ratio is also greater than 1:1. In illustrative embodiments, using a weight ratio from about 3:1 to 10:1 would be suitable. In preferred embodiments in which a heterogeneous catalyst incorporates nickel and rhenium, a useful support includes a mixed alumina-silica. Suitable catalysts are described in Assignee's co-pending U.S. Published Patent Application 2010/0087682, titled "LOW METAL CATALYST COMPOSITIONS INCLUDING ACIDIC MIXED METAL OXIDE AS SUPPORT" by Stephen W. King et al.

Additional catalysts suitable in the practice of the invention, including nickel, cobalt and copper catalysts, are also described in Assignee's co-pending U.S. Published Patent Application 2010/0137642 A1 titled "LOW METAL LOADED, ALUMINA SUPPORTED, CATALYST COMPOSITIONS AND AMINATION PROCESS" by Stephen W. King et al.

Catalysts can be heterogeneous, homogeneous, or a combination of these may be used. Homogeneous catalysts dissolve in the reaction medium. Illustrative homogeneous catalysts include the rhodium-based compound known as Wilkinson's catalyst and the iridium-based Crabtree's catalyst. Heterogeneous catalysts are solids that are caused to contact the reaction medium, which may be in liquid, gas or other fluid form.

Heterogeneous catalysts are preferred. Often, heterogeneous catalysts comprise one or more catalytic materials supported upon a suitable substrate. The substrate may be used in various shapes or combinations such as, for example, powder, particle, pellet, granule, extrudate, fiber, shell, honeycomb, plate, or the like. The particles can be regular in shape, irregular, dendritic, dendrite-free, or the like. Preferred supports are particulate in nature or powders.

Particulate support may have a so-called guest/host structure, which may be prepared by adsorbing or adhering fine (less than 100 micrometers, preferably less than 50 micrometers and most preferably less than 10 micrometer in size) nanoporous particles on coarser (greater than 30 mesh) particles. The smaller particles are referred to as guests, while the large particles supporting them are referred to as hosts. This small-particle-supported-on-a-larger-particle composite structure provides very high total exterior surface area while retaining the desirable gas passing characteristics, i.e., low pressure drop, of a coarser particle. In addition, by using smaller particles in constructing these composite particles, inexpensive, coarser particles can be used. Thus, very inexpensive, highly active catalyst particles can be prepared since the bulk of the volume of a catalyst bed may be taken up by the inexpensive, underlying, coarser particles.

The catalytically active material can be incorporated into or onto the guest and/or host particles. Often, the catalytically active material is incorporated mainly onto the guest material before or after the guest/host composite is formed. Guest/host structures and methods of making these are further described in U.S. Publication No. 2005/0095189 A1.

Preferably, the catalyst and/or the supported catalyst composition is calcined and reduced prior to use. Generally, calcining can occur in air or an inert atmosphere such as one based upon nitrogen, argon, carbon dioxide, combinations of these, and the like. Calcining can occur at a variety of elevated temperatures, such as a temperature up to about 1000° C., preferably about 200° C. to about 800° C. Reduction with hydrogen or a mixture of hydrogen and an inert (e.g., nitrogen) can occur at a variety of elevated temperatures, such as a temperature up to about 1000° C. preferably about 250-500° C.

A wide variety of materials may serve as suitable supports in the practice of the present invention. Representative examples include carbonaceous materials, silicaceous materials (such as silica), metal compounds such as metal oxides, combinations of these, and the like. Representative metal oxides include oxides of one or more of magnesium, aluminum, titanium, vanadium, chromium, manganese, iron, cobalt, nickel, copper, zinc, gallium, germanium, strontium, yttrium, zirconium, niobium, molybdenum, technetium, ruthenium, rhodium, palladium, silver, cadmium, indium, iron, tin, antimony, barium, lanthanum, hafnium, thallium, tungsten, rhenium, osmium, iridium, and platinum.

Examples of carbonaceous substances include activated carbon and graphite. Suitable activated carbon particles may be derived from a wide variety of source(s) including coal, coconut, peat, any activated carbon(s) from any source(s), combinations of at least two of these, and/or the like.

Catalytically active material may be incorporated into heterogeneous catalyst systems in a variety of ways. In some instances, a catalyst precursor is first provided on the support, and then the precursor can be converted into the catalyst itself afterward. Exemplary procedures are well known in the industry and include solution impregnation, precipitation, vapor deposition such as by physical or chemical vapor deposition techniques, and the like.

The amount of catalyst used in forming a cyclic polyamine using transamination is any amount, which is effective in producing the desire cyclic polyamine. For batch conditions, the quantity of catalyst may be in the range from about 0.1 to about 20 weight percent, preferably 1to 15 weight percent, of catalyst per 100 parts by weight of reactant(s) to be self-cyclized to form the desired triamine. In a continuous process, a typical strategy might involve causing a flow of reactants to contact a bed of heterogeneous catalyst particles. In such a case, the space velocity (usually expressed in units of gmol/(kg catalyst/hr) can be adjusted to balance factors such as production and selectivity.

When calculating the weight percent of catalyst for batch or continuous processes, only the actual amount of active catalytic substance is used to determine the weight percent of catalyst. For instance, in an exemplary embodiment, 100 parts by weight of heterogeneous catalyst particles might be used to treat a mixture containing 91 parts by weight of EDA and 9 parts by weight of 1,3-DAP. Other amines may or may not be present in the mix. The total amount of reactants is 100 parts by weight. The heterogenous catalyst particles might include 5 part by weight of Ni and 1 part by weight of Re as metals for a total of 6 parts by weight of catalyst. In this case, the batch reactor would include 6 parts by weight of the catalyst per 100 parts by weight of the reactants. For purposes of the present invention, if the catalyst is present as a molecule such as an oxide or the like, only the weight of the active metal catalyst constituent is used to determine the weight percent.

The reaction composition for transamination can be contacted with catalyst at any suitable temperature(s) that promote the ring closure reaction to produce the desired cyclic polyamine. Typically, the temperature is maintained below about 350° C., preferably below 300° C. Preferred temperatures are in the range from about 130° C. to about 180° C. for transamination. Below the preferred temperature ranges, the conversion to cyclic polyamine may be too slow to be practical for commercial scale production. Above the preferred temperature ranges, selectivity may be reduced to an undue degree, increasing the yield of by-products. In some instances, such by-products may have commercial value and be desirable as a consequence. In other instances, by-products constitute impurities as a practical matter.

Similarly, the reaction composition for transamination can be contacted with catalyst at any suitable pressure(s) that promotes the cyclization reaction to produce the desired cyclic polyamine. Preferably, the pressure is sufficient to maintain the reactor contents in a liquid state as the reaction proceeds. In many instances, the pressure will vary as the reaction proceeds. For instance, ammonia is a by-product of a typical transamination process. The production of ammonia causes the pressure generally to increase as the reaction proceeds. Ammonia and/or other pressure-increasing products can be removed from the reactor in order to keep the pressure below a desired threshold. Typically, the pressure is in the range from about 0 psi to about 5000 psi, preferably 10 psi to 3000 psi, more preferably 100 psi to 1000 psi. For transamination, pressures in the range of 400 psi to 800 psi are preferred.

The reaction composition for transamination can be contacted with catalyst at any suitable temperature(s) to promote the cyclic/acyclic product ratio, while minimizing byproduct formation. Typically, the temperature is maintained below about 350° C., preferably below 300° C. Preferred temperatures are in the range from about 130° C. to about 180° C. for transamination.

The above-described reaction conditions favor the formation of primarily cyclic products. The ratio of cyclic to acyclic products can be reduced by increasing the amount of the C3 component, or by changing the nature of the catalyst, pressure, temperature, etc. For example, product mixtures containing higher levels of acyclic, preferably linear, products are favored when using reactant mixtures in which the majority of the reactants have ternary or higher spacing between the nitrogen-containing functional groups. In this instance, the amount of a second reactant that has a binary spacing between nitrogen-containing functional groups comprises less than about 50 mole %, preferably less than about 25 mole %, more preferably is about 10 mole %.

In many embodiments, the amine mixture used as a starting reaction material for transamination will be in liquid form such that no additional solvent is needed. Indeed, in many instances it may be preferred to carry out the desired reaction in the absence of solvent. However, one or more solvents may be used if desired. A variety of solvents or combinations of solvents may be used. Desirably, the solvent is not unduly reactive with the higher amine reactant(s) or cyclic polyamine product(s) and does not unduly decompose under the reaction conditions. Some examples of solvents that could be used include saturated hydrocarbons such as pentane, hexane, octane, nonane, decane, or the like; aromatic hydrocarbons such as toluene, benzene, xylene, ether, combinations of these, and the like. Alcohols are desirably avoided, as many of these are capable of reacting with the amine reactants and/or products. If present, the amount of solvent used may vary over a wide range. In a typical instance, the solvent may constitute from about 5 to about 98 weight percent, desirably 10 to 80 weight percent, of the mixture. Optionally when solvent is used, the reaction medium can be diluted to favor intramolecular reactions and, hence, cyclization, relative to intermolecular interactions.

The reactant composition for transamination optionally may include hydrogen. When hydrogen is used, the level of hydrogen can be adjusted to favor ring closure. Generally, a lower hydrogen concentration favors ring closure. From 0 to about 50 mole percent, desirably 0.1 to 25 mole percent of hydrogen per mole of reactants would be suitable.

The following Assignee co-pending U.S. patent applications describe technology relating to catalysts and/or transamination: U.S. Pat. Pub. No. 2010/0137642; U.S. Pat. Pub. No. 2010/0087682; U.S. Pat. Pub. No. 2010/0087683; U.S. Pat. Pub. No. 2010/0087684; U.S. Pat. Pub. No. 2010/0094007; U.S. Pat. Pub. No. 2010/0094008; and U.S. Pat. Pub. No. 2010/0087681. Each is incorporated herein by reference in its respective entirety for all purposes.

The present invention will now be further described with reference to the following illustrative examples.

Catalyst Preparation

The catalyst was prepared by using precursor salts of the metals (nickel nitrate and ammonium perrhenate) dissolved in 70-80 C water to form an impregnation solution. The final volume of the impregnation solution was adjusted to equal the adsorption volume required for the number of times that the carrier was impregnated, and the quantities of the precursor salts were those calculated to give the desired metal compositions. The carrier was impregnated to incipient wetness by the addition of the appropriate amount of impregnation solution and gently agitated until all the liquid was adsorbed. The sample was then placed in a muffle furnace and calcined in air for one hour at 340° C. When the material had cooled, additional impregnations were performed until all of the solution had been added. A calcination step at 340° C. was done after each impregnation. Prior to use, the catalyst compositions were reduced in hydrogen by ramping the temperature at 3 C/min to 230° C., holding at this temperature for one hour, and then ramping at 3° C./min to 340° C., and holding for 3 hours. The catalyst composition was allowed to cool under hydrogen to ambient temperature, after which it was stabilized by adding a flowing stream of 1% oxygen in nitrogen until the exotherm ceased. At no time was the exotherm allowed to exceed about 70 C. The catalyst has a nominal loading of 6.8 wt. percent Ni and 1.8 wt. percent Re on an $Al_2O_3/SiO_2$ (80:20), $\frac{1}{16}$" extrudate (SA-153 $m^2/g$).

Reaction Conditions

The reactions were conducted in a 2 L high-pressure 316SS autoclave (Autoclave Engineers) equipped with a magnetic stirrer, a dip tube for sampling, and a catalyst basket. The catalyst was charged to the catalyst basket and activated overnight with flowing hydrogen at 180° C. The autoclave was cooled to room temperature, and the liquid reactants (e.g., 1,3-DAP and EDA) charged by pressure, taking care not to admit air. The autoclave was brought to operating pressure with hydrogen, and heated to operating temperature with stirring. Samples were taken hourly via a dip tube and analyzed by GC. Prior to analysis, ammonia (if present) was allowed to evaporate. Gas Chromatography analyses of the product mixtures were done on a DB-5MS, 30 m×0.32 mm ID×1 micron column. Peaks were identified with the aid of GC/mass spec. All GC peaks represent % by weight of the designated product in the mixture.

EXAMPLE 1

A 1:1 molar feed of EDA and 1,3-DAP was charged to the 2 L high pressure autoclave described above. The reactor was heated at 150-155° C. Samples were obtained every hour for 6 hours and analyzed as described above. The results are given in Table 1. Table 1 shows that a high level of cyclic diamine products were formed (e.g., PIP and hPIP) in the product mixture. The cyclic content increases in the product mixture as the conversion of EDA and 1,3-DAP increases.

TABLE 1

Autoclave Run
EDA/1,3-diaminopropane, 1:1 molar (45:55, wt)
500 grams liquid amine
50 grams catalyst
128 PSIG Hydrogen

| Temp, ° C. | | 150 | 150 | 150 | 155 | 155 | 155 |
|---|---|---|---|---|---|---|---|
| Time, hrs | | 1 | 2 | 3 | 4 | 5 | 6 |
| EDA conv | | 18.04 | 30.08 | 40.41 | 57.90 | 65.55 | 79.73 |
| 1,3-DAP conv | | 6.93 | 11.44 | 15.57 | 23.25 | 27.38 | 35.37 |
| GC results | | | | | | | |
| EDA | 42.34 | 34.70 | 29.60 | 25.23 | 17.83 | 14.59 | 8.58 |
| 1,3 diaminopropane | 57.39 | 53.41 | 50.82 | 48.45 | 44.04 | 41.67 | 37.09 |
| PIP | | 0.45 | 1.04 | 1.83 | 3.96 | 5.15 | 8.24 |
| Homopiperazine | | 0.64 | 1.27 | 2.03 | 4.12 | 5.55 | 10.25 |
| DETA | | 4.59 | 6.93 | 8.33 | 8.91 | 8.34 | 5.48 |
| N-(2-aminoethyl)-1,3-propanediamine | | 2.60 | 4.35 | 5.77 | 7.77 | 8.36 | 8.20 |

TABLE 1-continued

Autoclave Run
EDA/1,3-diaminopropane, 1:1 molar (45:55, wt)
500 grams liquid amine
50 grams catalyst
128 PSIG Hydrogen

| | | | | | | | |
|---|---|---|---|---|---|---|---|
| Dipropylenetriamine | | 1.24 | 1.67 | 1.93 | 2.13 | 2.12 | 1.75 |
| AEP | | | | 0.16 | 0.47 | 0.71 | 1.40 |
| L-TETA | | | 0.66 | 1.09 | 1.82 | 2.03 | 1.89 |
| N-(3-aminopropyl)-dethylenetriamine | | | | 0.59 | 1.23 | 1.58 | 2.16 |
| L-TEPA | | | | 0.13 | 0.39 | 0.48 | 0.60 |
| N-(3-aminopropyl)-triethylenetetramine | | | | | 0.15 | 0.22 | 0.41 |
| Others | 0.27 | 2.39 | 3.65 | 4.46 | 7.20 | 9.22 | 13.97 |

EXAMPLE 2

A 1:3 molar feed of EDA and 1,3-DAP was charged to the 2 L high pressure autoclave described above. The reactor was heated at 130-135° C. Samples were obtained every hour for 6 hours, and analyzed as described above. The results are given in Table 2. This example shows a lower level of cyclic products formed (e.g., PIP and hPIP) when a 1:3 molar ratio of EDA to DAP is used compared to the example above.

TABLE 2

Autoclave Run
EDA/1,3-diaminopropane, 1:3 molar (21:79, wt)
424 grams liquid amine
50 grams catalyst
150 PSIG hydrogen

| | | | | | | | |
|---|---|---|---|---|---|---|---|
| Temp, ° C. | | 130 | 130 | 135 | 135 | 135 | 135 |
| Time, hrs | 0 | 1 | 2 | 3 | 4 | 5 | 6 |
| EDA conv | | 13.68 | 23.22 | 35.86 | 47.66 | 56.33 | 81.33 |
| 1,3-DAP conv | | 10.18 | 18.17 | 28.54 | 38.58 | 46.40 | 53.51 |
| GC results | | | | | | | |
| propylamine | | | | 0.017 | 0.028 | 0.043 | 0.053 |
| EDA | 17.473 | 15.082 | 13.416 | 11.207 | 9.146 | 7.631 | 3.263 |
| 1,3 diaminopropane | 82.344 | 73.962 | 67.379 | 58.84 | 50.576 | 44.137 | 38.285 |
| Piperazine | | 0.021 | 0.56 | 0.127 | 0.236 | 0.35 | 0.478 |
| Homopiperazine | | | | 0.307 | 0.594 | 0.901 | 1.252 |
| N-propyl-1,3-diaminopropane | | | | 0.101 | 0.132 | 0.156 | 0.178 |
| DETA | | 0.46 | 0.782 | 1.091 | 1.301 | 1.37 | 1.358 |
| N-(2-aminoethyl)-1,3-propanediamine | | 4.084 | 6.893 | 10.002 | 12.306 | 13.497 | 14.087 |
| dipropylenetriamine | | 5.44 | 9.154 | 13.343 | 16.678 | 18.672 | 20.019 |
| N-(3-aminopropyl)-diethylenetriamine | | | 0.232 | 0.563 | 0.976 | 1.346 | 1.693 |
| N-(2-aminoethyl)dipropylenetriamine | | | 0.804 | 1.871 | 3.264 | 4.552 | 5.831 |
| tripropylenetetramine | | | 0.663 | 1.614 | 2.837 | 3.985 | 5.159 |
| Others | 0.183 | 0.951 | 0.117 | 0.917 | 1.926 | 3.36 | 8.344 |

What is claimed is:

1. A method of making a cyclic polyamine-containing product mixture comprising the steps of:

(a) providing a reaction composition comprising one or more nitrogen-containing compounds having a binary component that has at least two non-tertiary amine groups separated from one another by a binary carbon atom spacing (C2 spacing) and, a second component comprising a second nitrogen-containing compound having (i) at least two non-tertiary amine groups separated from one another by a ternary carbon atom spacing (C3 spacing), (ii) at least two nitrile functionalities separated by a unitary carbon atom spacing (C1 spacing), (iii) at least one nitrile functionality and one non-tertiary amine functionality separated from one another by a binary carbon atom spacing (C2 spacing), or (iv) a combination thereof; and (b) subjecting the reaction composition to a transamination reaction in the presence of a hydrogenation/ dehydrogenation catalyst to obtain the cyclic polyamine-containing mixture.

2. A method of making homopiperazine and/or homopiperazine moieties comprising the steps of:

(a) providing a reaction composition comprising (i) $H_2NCH_2CH_2NHCH_2CH_2CH_2NH_2$, or $H_2NCH_2CH(CH_3)NHCH_2CH_2CH_2NH_2$, or a mixture thereof, or (ii) a mixture of 1,3-diaminopropane and ethylenediamine; or (iii) a mixture of 1,3-diaminopropane and 1,2-propanediamine; and (b) subjecting the reaction composition to a transamination reaction in the presence of a hydrogenation/dehydrogenation catalyst to obtain a product mixture comprising homopiperazine and/or homopiperazine moieties.

3. The method of claim 1, wherein the binary component comprises a polyamine having by the formula

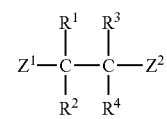

FORMULA I wherein $Z^1$ and $Z^2$ are independently primary or secondary amines; and $R^1$, $R^2$, $R^3$, and $R^4$ are, independently, H or substituted and unsubstituted hydrocarbyl.

4. The method of claim 1, wherein the second component has a formula selected from

FORMULA III

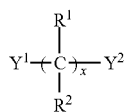

wherein $Y^1$ and $Y^2$ are each CN;
x is an integer of from 1 to about 10;
$R^1$ and $R^2$ are, independently, H or substituted and unsubstituted hydrocarbyl;
or the formula

FORMULA IV

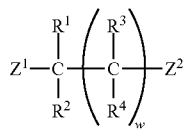

wherein $Z^1$ and $Z^2$ are independently primary or secondary amines;
$R^1$, $R^2$, $R^3$ and $R^4$ are, independently, H or substituted and unsubstituted hydrocarbyl; and
w is an integer of 2 or more.

5. The method of claim 1, wherein the polyamine product mixture comprises a mixture of congeners of polyamine products.

6. The method of claim 1, wherein the binary component and the second component are at a molar ratio in the range of about 0.1:1 to about 10:1, respectively.

7. The method of claim 6, wherein the molar ratio is about 1:1.

8. The method of claim 1, wherein the binary component and the second component are at a molar ratio of less than about 1:1, , respectively.

9. The method of claim 1, wherein the catalyst comprises at least one of Pt, Pd, Rh, Re, Ru, Ni, Cu, Co and combinations thereof.

10. The method of claim 1, wherein the transamination occurs in the presence of a heterogeneous catalyst comprising Ni and Re.

11. The method of claim 1, wherein the reaction composition further comprises from about 0.1 to about 50 mole percent of hydrogen per mole of reactants.

12. A mixture of polyamines obtained by the method of claim 1.

13. A method of making a cyclic polyamine-containing product mixture comprising the steps of:
providing a reaction composition comprising one or more nitrogen-containing compounds having a binary component that has at least two non-tertiary amine groups separated from one another by a binary carbon atom spacing (C2 spacing) and, optionally, a second component that has at least two nitrogen containing groups separated from one another by a second carbon atom spacing,; and
subjecting the reaction composition to a transamination reaction in the presence of a hydrogenation/ dehydrogenation heterogeneous catalyst comprising Ni and Re to obtain the cyclic polyamine-containing mixture.

* * * * *